(12) United States Patent
Saydar et al.

(10) Patent No.: US 9,854,843 B2
(45) Date of Patent: Jan. 2, 2018

(54) VAPORIZER (71) Applicant: Haze Industries, Inc., Alpharetta, GA (US)

(72) Inventors: Taylan Saydar, Alpharetta, GA (US); Brian VanHiel, Smyma, GA (US); David Buenger, Roswell, GA (US); Baker Whisnant, Coral Springs, FL (US)

(73) Assignee: HAZE INDUSTRIES, INC., Alpharetta, GA (US)

( * ) Notice: Subject to any disclaimer, the term of this patent is extended or adjusted under 35 U.S.C. 154(b) by 733 days.

(21) Appl. No.: 14/296,393

(22) Filed: Jun. 4, 2014

(65) Prior Publication Data
US 2015/0040926 A1 Feb. 12, 2015

Related U.S. Application Data (60) Provisional application No. 61/863,872, filed on Aug. 8, 2013.

(51) Int. Cl.
| A24F 47/00 | (2006.01) |
| B02C 18/12 | (2006.01) |
| B02C 18/18 | (2006.01) |
| B02C 19/00 | (2006.01) |
| A61M 15/00 | (2006.01) |
| A61M 11/04 | (2006.01) |

(52) U.S. Cl.
CPC ......... *A24F 47/008* (2013.01); *A61M 11/042* (2014.02); *A61M 11/045* (2014.02); *A61M 15/00* (2013.01); *B02C 18/12* (2013.01); *B02C 18/186* (2013.01); *B02C 19/0056* (2013.01); *A61M 2202/066* (2013.01)

(58) Field of Classification Search
CPC ...................................................... A24F 47/008
USPC .................................................. 392/386–406
See application file for complete search history.

(56) References Cited

U.S. PATENT DOCUMENTS

| 5,144,962 | A * | 9/1992 | Counts ................. A24F 47/008 128/200.14 |
| 5,564,442 | A | 10/1996 | MacDonald et al. |
| 6,789,789 | B2 | 9/2004 | Randive et al. |
| D654,160 | S | 2/2012 | Yomtov |
| D656,230 | S | 3/2012 | Robinson et al. |
| D664,636 | S | 7/2012 | Robinson et al. |
| D677,774 | S | 3/2013 | Postma |
| D690,002 | S | 9/2013 | Storey et al. |
| D705,918 | S | 5/2014 | Robinson et al. |
| 8,739,788 | B2 | 6/2014 | Yomtov |
| D720,497 | S | 12/2014 | Alima |
| D725,310 | S | 3/2015 | Eksouzian |

(Continued)

*Primary Examiner* — Eric Yaary
(74) *Attorney, Agent, or Firm* — Minh N. Nguyen; Next ip Law Group LLC (57) ABSTRACT

Vaporizers are provided. A representative vaporizer includes a power source; a heating element that is electrically coupled to the power source; multiple chambers that are coupled to the heating element and are configured to vaporize a substance that is placed within the multiple chambers; an inner tube that is coupled to the multiple chambers and is configured to allow the vaporized substance to exit therefrom; and a housing that houses the power source, heating element, inner tube, and multiple chambers.

15 Claims, 7 Drawing Sheets

(56) References Cited

U.S. PATENT DOCUMENTS

| | | | |
|---|---|---|---|
| 2009/0302019 A1* | 12/2009 | Selenski | A24F 47/008 219/201 |
| 2011/0305606 A1 | 12/2011 | Kilby | |
| 2012/0152244 A1 | 6/2012 | Yomtov | |
| 2012/0255546 A1 | 10/2012 | Goetz et al. | |
| 2013/0139813 A1 | 6/2013 | Storz | |
| 2013/0298905 A1 | 11/2013 | Levin et al. | |
| 2014/0000638 A1* | 1/2014 | Sebastian | A24F 47/008 131/328 |
| 2014/0283824 A1 | 9/2014 | Wheelock et al. | |
| 2015/0122277 A1* | 5/2015 | Frobisher | A24D 3/04 131/329 |

\* cited by examiner

VAPORIZER

CROSS REFERENCE TO RELATED APPLICATIONS

This application claims the benefit of U.S. provisional application entitled, "VAPORIZER," having Ser. No. 61/863,872, filed on Aug. 8, 2013, all of which are entirely incorporated herein by reference.

TECHNICAL FIELD

The present disclosure is generally related to vaporizer and, more particularly, is related to systems and methods for vaporizing substance in multiple chambers.

BACKGROUND

Vaporizers are becoming more popular for various reasons. One reason is that vaporizers produce less carcinogens than regular cigarettes. This is especially beneficial patients who use cannabis for medical reasons.

Desirable in the art is an improved vaporizer that would improve upon the conventional vaporizer.

SUMMARY

Vaporizers are provided. A representative vaporizer includes a power source; a heating element that is electrically coupled to the power source; multiple chambers that are coupled to the heating element and are configured to vaporize a substance that is placed within the multiple chambers; an inner tube that is coupled to the multiple chambers and is configured to allow the vaporized substance to exit therefrom; and a housing that houses the power source, heating element, inner tube, and multiple chambers.

Other systems, devices, methods, features of the invention will be or will become apparent to one skilled in the art upon examination of the following figures and detailed description. It is intended that all such systems, devices, methods, features be included within the scope of the invention, and be protected by the accompanying claims.

BRIEF DESCRIPTION OF DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, the reference numerals designate corresponding parts throughout the several views. While several embodiments are described in connection with these drawings, there is no intent to limit the disclosure to the embodiment or embodiments disclosed herein. On the contrary, the intent is to cover all alternatives, modifications, and equivalents.

DETAILED DESCRIPTION

Exemplary vaporizers are first discussed with reference to the figures. Although these vaporizers are described in detail, they are provided for purposes of illustration only and various modifications are feasible.

Figure 1:
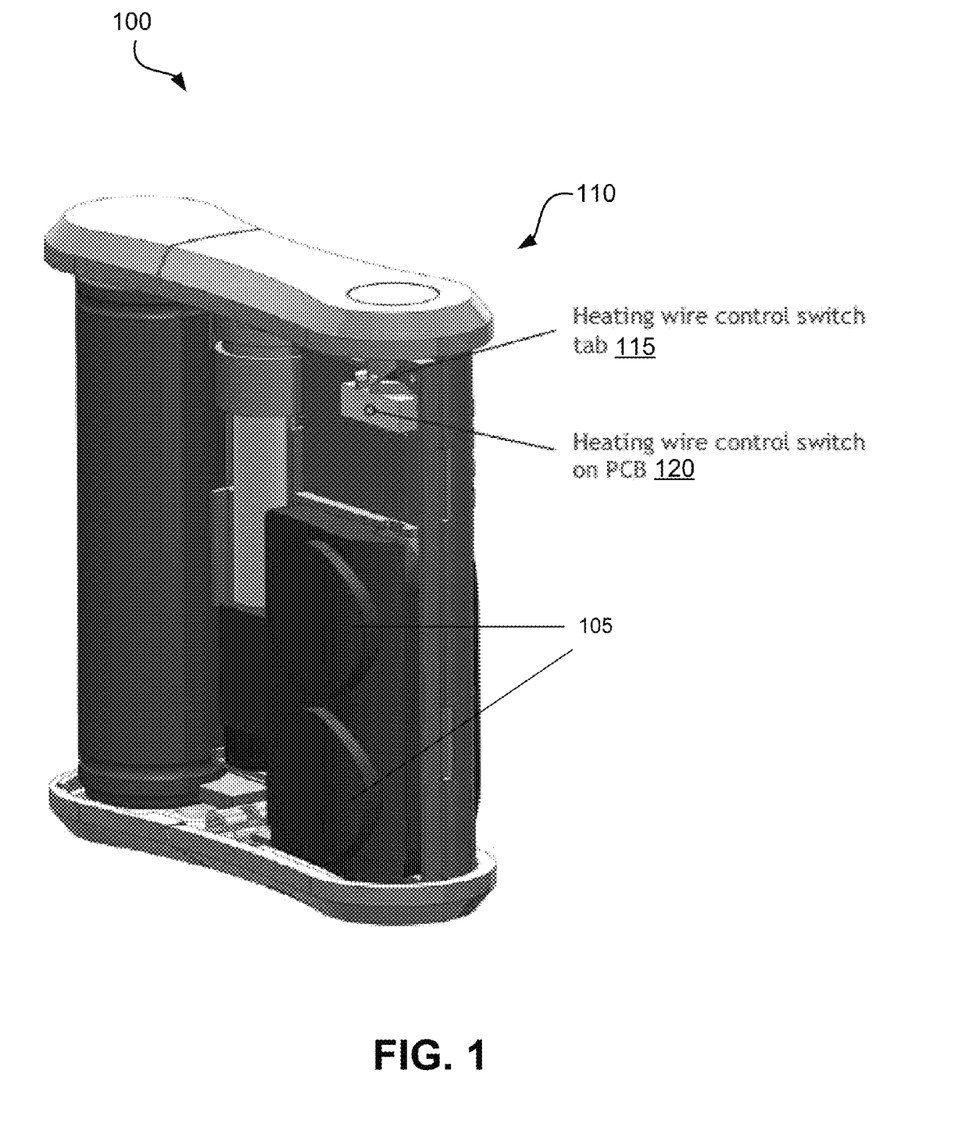
FIG. 1 is a perspective view of a vaporizer in accordance with an embodiment of the invention.

A new, novel and useful vaporizer 100 that is disclosed herein can be a compact unit that slightly bigger than a business card. FIG. 1 is a perspective view of the vaporizer 100 in accordance with an embodiment of the invention. The vaporizer 100 includes at least one internal chamber 105. In this example, the vaporizer 100 includes two internal chambers 105 that can optimize vaporization, lessen heat up time inside the chambers and provide the user with two chambers to draw from at different times. The chambers 100 can be made of a thermal conductive material, such as stainless steel, and can be shaped as bowls, which are cylindrical, but can be designed to have any geographical shapes as long as the chambers 100 can contain the herbs for vaporization. The vaporizer 100 further includes controls 110 that rotate at least one internal structure 220 (FIG. 2) that aligns/misaligns air pathways while actuating electronic switches 115, 120. The two chambers 105 can be designed to be contacting with the heating elements (aka "conduction method") to heat, for example, Cannabis oil and wax, and/or to not contact with the heating element (aka "convection method") to heat, for example, herbs. The vaporizers can be designed to have two chambers 105, both using conduction method, both using convection method, or one using conduction method and the other using convection method.

Figure 2:
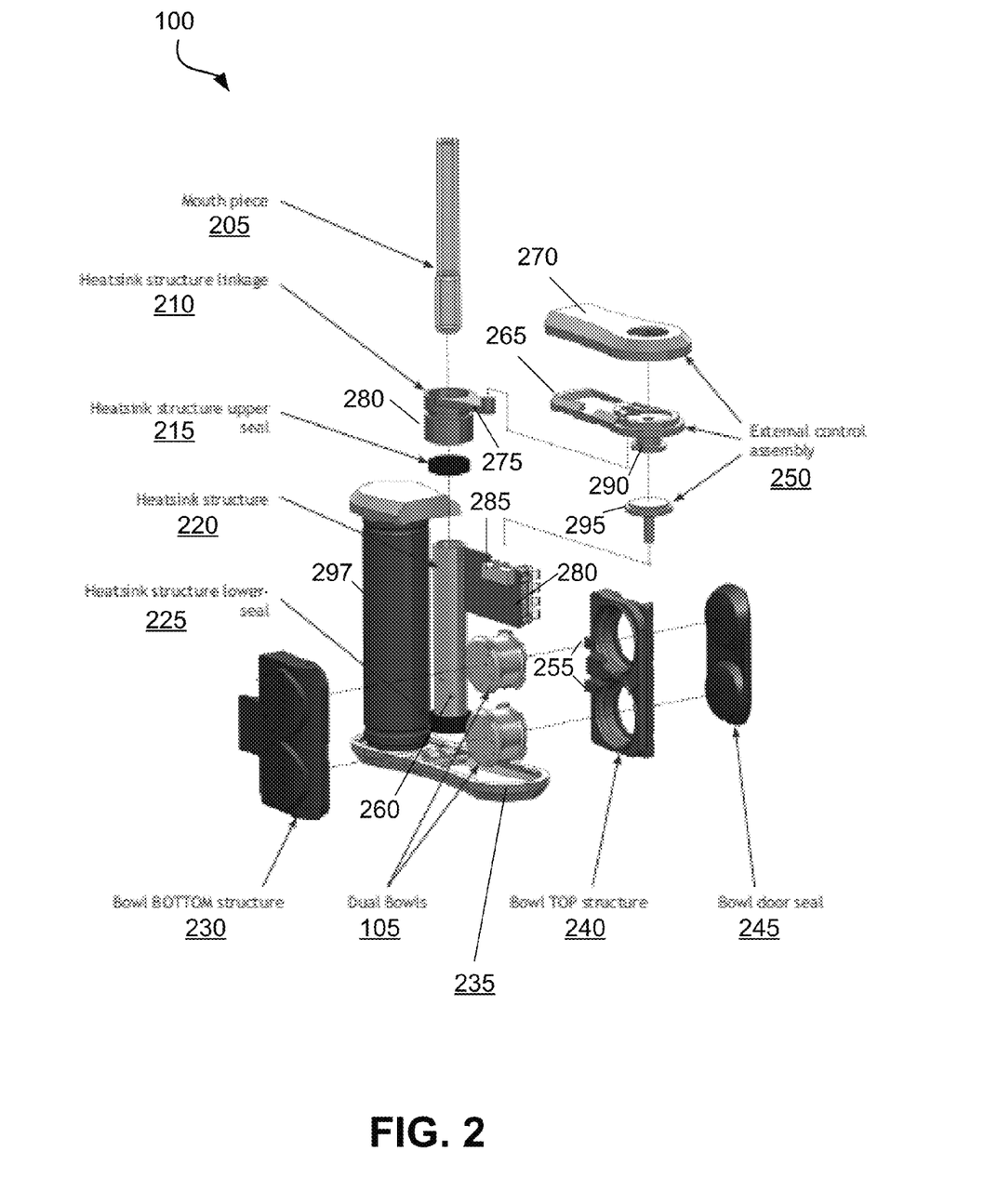
FIG. 2 is an exploded pre-assembly view of a vaporizer in accordance with an embodiment of the invention.

FIG. 2 is an exploded pre-assembly view of the vaporizer 100 in accordance with an embodiment of the invention. In this figure, the rotatable internal structure 220 is referred to as a "heatsink structure" that is an elongated tubular structure. The rotatable internal structure 220 is mechanically coupled at the top end of the structure 220 to a heatsink structure upper seal 215 and a heatsink structure linkage 210. At the bottom end of the structure 220, the rotatable internal structure 220 is mechanically coupled to a heatsink structure lower seal 225, which rest on a base cover 235 of the vaporizer 100. The internal herbal chambers 100 is placed within a chamber container 230, 240, 245 that stores and positions the internal herb chambers 100 vertically along the side of the rotatable internal structure 220.

The lever structure 265 includes a cylindrical base 280 that couples to the rotatable internal structure 220 at a proximal end and an arm 275 at a distal end of the base 280. The arm 275 includes a bar attached on top and at the distal end of the arm 275. The heatsink structure linkage 210 is mechanically coupled to a lever structure 265 via the arm 275, which rotates horizontally to the left or right with respect to the rotatable internal structure 220. The rotation of the lever structure is further described in connection to FIG. 3. The lever structure 265 is covered by a lever cover 270, which also provides structural support to the lever structure 265 to be able to rotate horizontally.

The lever structure 265 includes a switch linkage 290 which mechanical couples to a switch/chip assembly 280, 285 at a distal end of the switch linkage 290. The switch/chip assembly 280, 285 includes a switch 280 that is electrically coupled to a chip control device 285, which is designed to provide power to heating elements associated with at least one of the internal chambers 105. For example, the chip control device 285 is designed to connect electrical components to a power source 297 (e.g., external battery) to the top internal chamber 105 in a left position or the bottom internal chamber 105 in a right position of the lever structure 265. The chip control device 285 can be designed to disconnect electrical components to the power source 297 in an "off" position of the lever structure 265. In the off position of the lever structure 265, a distal end of the lever structure 265 is pointing at the rotatable internal structure 220, such as that shown in FIG. 1.

A push bottom 295 is placed between the lever structure 265 and the lever cover 270 and mechanically coupled to switch/chip assembly 280, 285 via an extending bar. Responsive to pushing in the push button 295, the push button actuates a power control switch (not shown) to provide power to the chip assembly 280. The operations of the vaporizer 100 is further described in FIGS. 3 and 4. A user can further push the push button following the "power on" push to instruct the chip control device 285 to adjust temperatures of the heating elements associated with at least one of the internal chambers 105. For example, after the user push the push button to power on the vaporizer 100, the user can push the push button a second, third, and fourth time to adjust the heating elements to heat at three different temperatures.

The chamber container 305 (FIG. 3) has extending bars 255 that couples to the rotatable internal structure 220 and aligns/misaligns with corresponding holes 260 at the rotatable internal structure 220. The extending bars 255 has a bore creating an air path from a distal end to a proximal end of the extending bars 255, such that air can travel to chamber container 230, 240, 245. In this example, one of the corresponding holes 260 are aligned with one of the extending bars 255 to provide an air pathway between one of the chambers 105 and the rotatable internal structure 220 and the other corresponding hole 260 are misaligned with the other extending bar 255, such that the other extending bar 255 is adjacent to the sidewalls of the rotatable internal structure 220.

Figure 3:
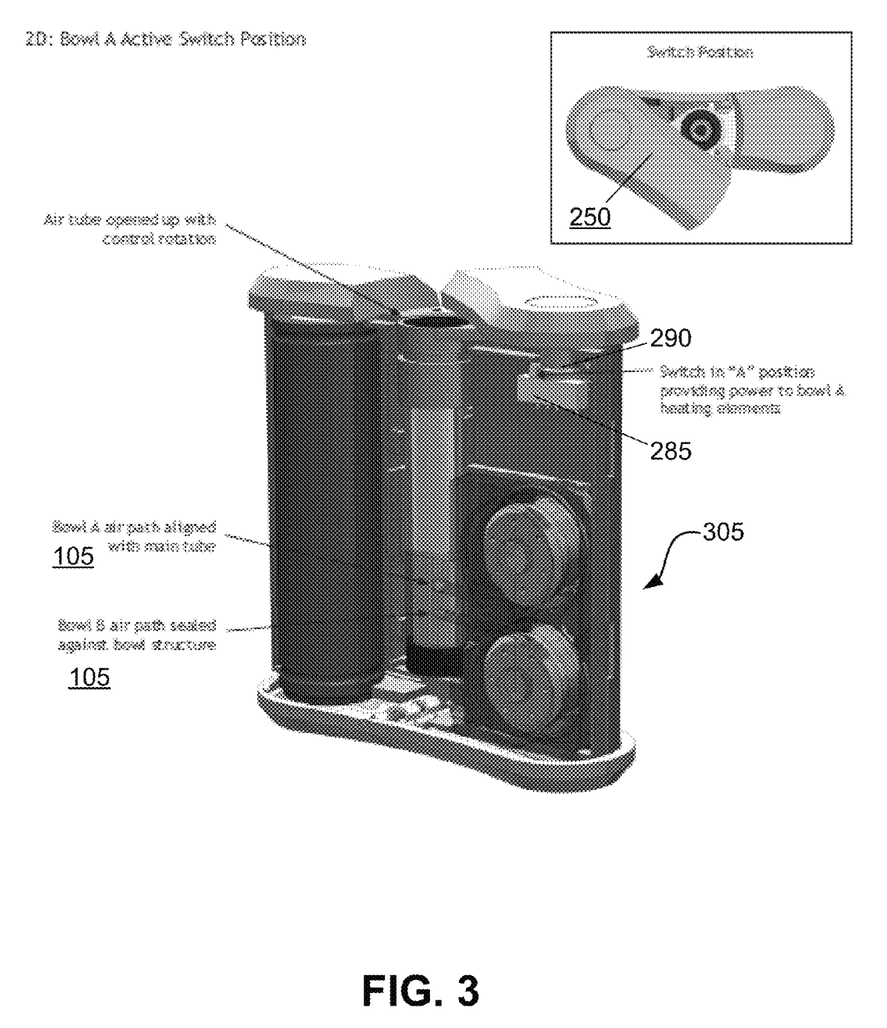
FIG. 3 is a diagram that shows the alignment and misalignment of extending bars and the corresponding holes in accordance with an embodiment of the invention.

FIG. 3 is a diagram that shows the alignment and misalignment of the extending bars 255 and the corresponding holes 260 in accordance with an embodiment of the invention. In this example, the lever structure 265 is in a left position from the perspective of the rotatable internal structure 220. In the left position of the lever structure 265, the switch linkage 290 turns the switch 285 to a left direction, which in this example facilitates providing power to the heating elements associated with the bowl A (top chamber 105).

Also in the left position of the lever structure 265, the arm 275 of the heatsink structure linkage 210 rotates to the left, also rotating the rotatable internal structure 220 in a counterclockwise direction from a top view perspective. The top hole 260 on the rotatable internal structure 220 is aligned with the top extending bar 255 to create an air pathway to a section of the chamber container 305 containing bowl A. The bottom hole 260 on the rotatable internal structure 220 is misaligned with the bottom extending bar 255 to block an air pathway to a section of the chamber container 305 containing bowl B. The bottom extending bar 255 is sealed against the rotatable internal structure 220.

Figure 4:
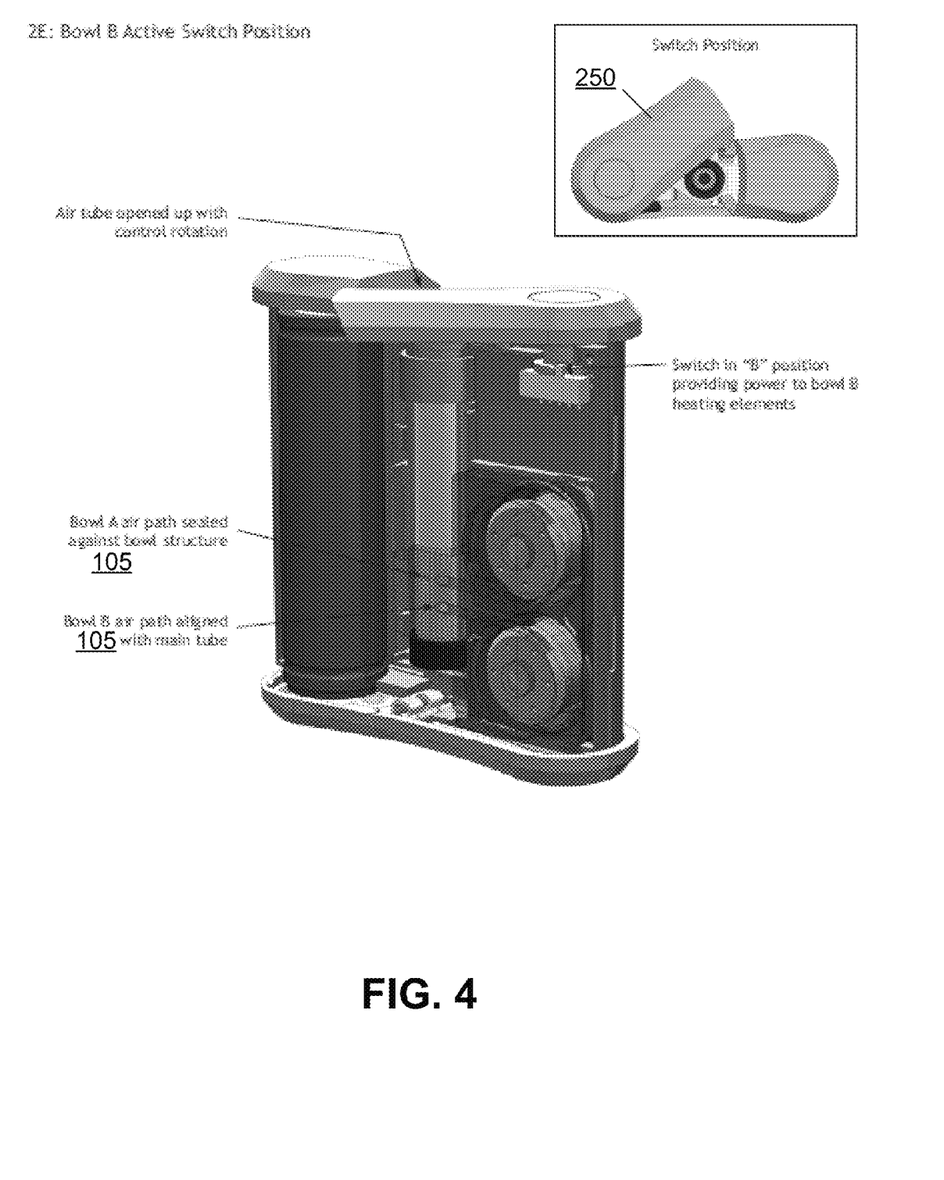
FIG. 4 is a diagram that shows the alignment and misalignment of extending bars and the corresponding holes in accordance with an embodiment of the invention.

FIG. 4 is a diagram that shows the alignment and misalignment of the extending bars 255 and the corresponding holes 260 in accordance with an embodiment of the invention. In this example, the lever structure 265 is in a right position from the perspective of the rotatable internal structure 220. In a right position of the lever structure 265, the switch linkage 290 turns the switch 285 to a right direction, which in this example facilitates providing power to the heating elements associated with the bowl B (bottom chamber 105).

Also in the right position of the lever structure 265, the arm 275 of the heatsink structure linkage 210 rotates to the left, also rotating the rotatable internal structure 220 in a clockwise direction from a top view perspective. The bottom hole 260 on the rotatable internal structure 220 is aligned with the bottom extending bar 255 to create an air pathway to a section of the chamber container 305 containing bowl B. The top hole 260 on the rotatable internal structure 220 is misaligned with the top extending bar 255 to block an air pathway to a section of the chamber container 305 containing bowl A.

Both extending bars 255 can be misaligned with the corresponding holes 260 and sealed against the rotatable internal structure 220 in a closed position of the lever structure 265, such as that shown in FIG. 1. In either the left or right position of the lever structure 265, the rotatable internal structure 220 is opened such that an air tube 205 (FIG. 2) can be extracted out of the rotatable internal structure 220. The air tube 205 can be made of durable glass or metal, for example.

Figure 5:
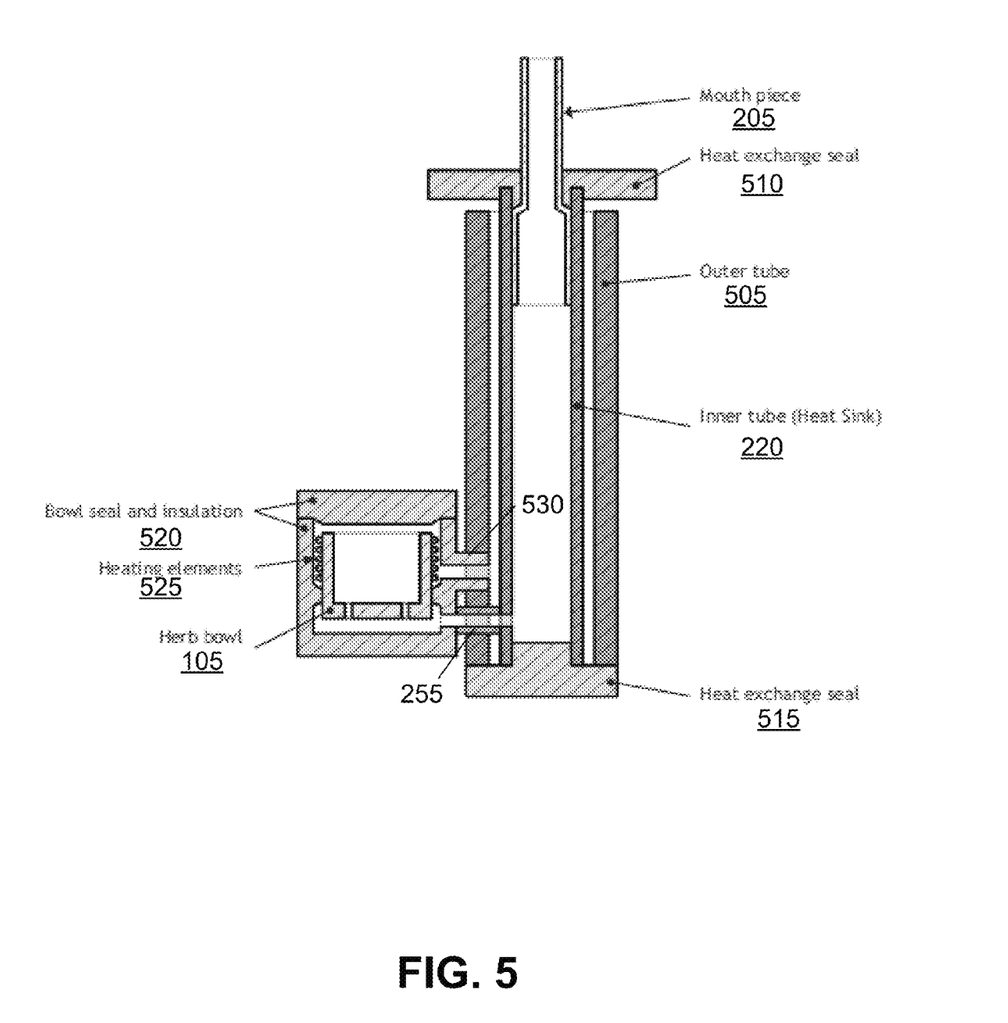
FIG. 5 is a diagram that illustrates a cross-sectional view of a vaporizer that directs air movement inside the vaporizer where outgoing air preheats ingoing air in accordance with an embodiment of the invention.

FIG. 5 is a diagram that illustrates a cross-sectional view of a vaporizer 100 that directs air movement inside the vaporizer 100 where outgoing air preheats ingoing air in accordance with an embodiment of the invention. External air enters an assembly that includes two concentric tubes 505, 220. An internal, thin gauge, highly conductive tube 220 is located closely to a thicker less external conductive tube 505. The internal tube 220 is place between a bottom seal 515 and a top heat exchange seal 510, which has an opening for a mouth piece 205 therethrough. A bowl seal and insulation 520 is mechanically coupled to the external tube 505 via extending bar 530 and the internal tube 220 via extending bar 255. The bowl seal and insulation 520 is designed to contain an herbal chamber 105. Heating elements 525 heat up the herbal chamber 105 for vaporizing herbs, for example. The airflow and heat exchange inside the vaporizer 100 is further described in FIG. 6.

Figure 6:
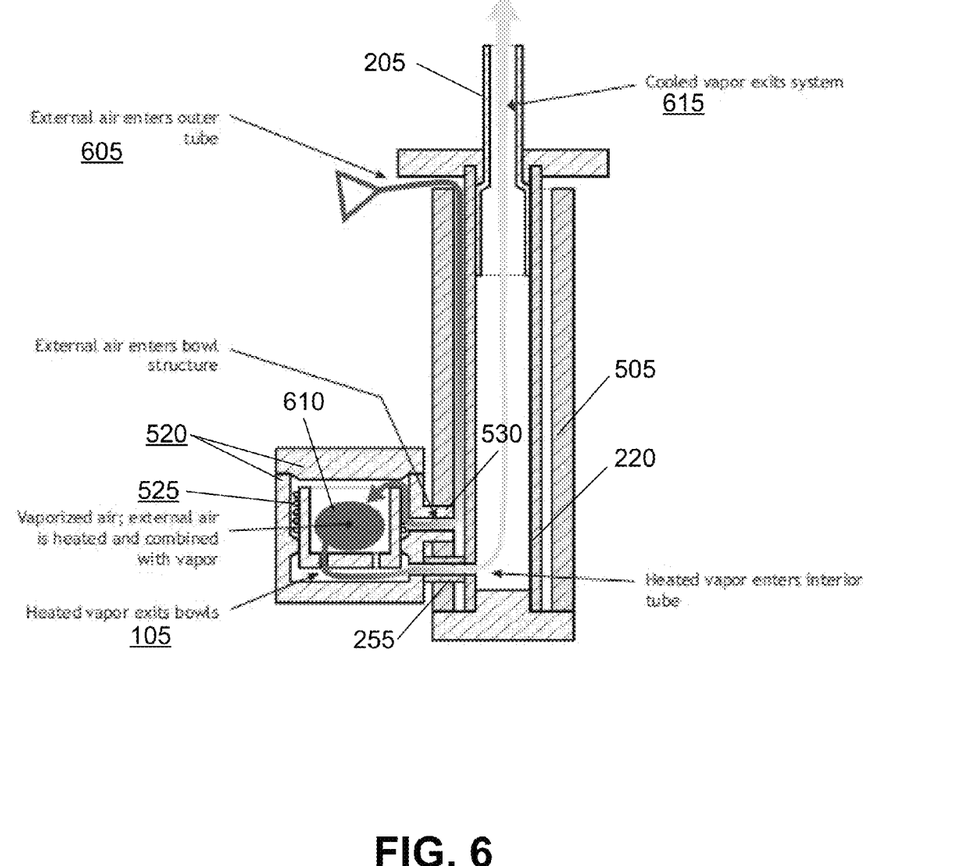
FIG. 6 is a diagram that illustrates a cross-sectional view of a vaporizer that shows air movement inside the vaporizer where outgoing air preheats ingoing air in accordance with an embodiment of the invention.

FIG. 6 is a diagram that illustrates a cross-sectional view of a vaporizer 100 that shows air movement inside the vaporizer 100 where outgoing air preheats ingoing air in accordance with an embodiment of the invention. Cool external air 605 enters the assembly at an opening at the distal end of and between the area of the internal tube 220 and the external tube 505. The external air 605 travels towards the bowls from the distal end to the proximal end of the internal tube 220 and the external tube 505. The external air 605 enters the bowl seal and insulation 520 via the external bar 530, passing over heating elements on its way into the herbal chamber 105. The heated air 605 vaporizes herbs, for example, resulting in heated vapor inside the herbal chamber 105. The heated vapor 610 exits the herbal chamber 105 and enters the inner tube via extending bar 255 on its way out of the internal tube 220 and mouth piece 205.

Figure 7:
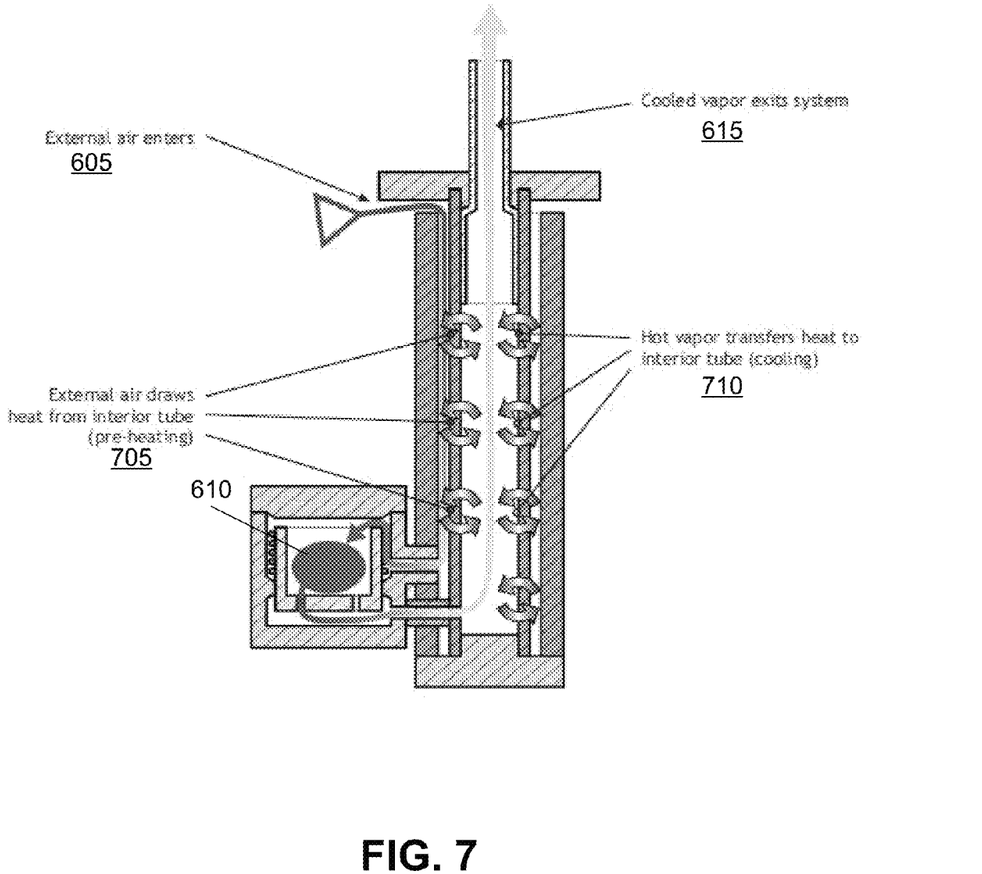
FIG. 7 is a diagram that illustrates a cross-sectional view of a vaporizer that shows heat transfer inside the vaporizer in accordance with an embodiment of the invention.

FIG. 7 is a diagram that illustrates a cross-sectional view of a vaporizer 100 that shows heat transfer inside the vaporizer 100 in accordance with an embodiment of the invention. As the heated vapor 610 travels through the internal tube 220, the heated vapor 610 transfers heat to the internal tube 220. In other words, the internal tube 220 absorbs some of the heat of the heated vapor 610, cooling the heated vapor 610. Cooled vapor 615 exits out of the internal tube 220 and mouth piece 205. Also, the heat absorbed by the internal tube 220 is passed to the incoming external air 605 in effect preheating the incoming external air 605. This method aids in more efficient heating of the air inside the herbal chamber 105, conserves battery energy and cools vapor exited the internal tube 220 and mouth piece 205.

FIG. 8 is an exploded pre-assembly view of a vaporizer 800 having an integrated grinder unit 805 in accordance with an embodiment of the invention. The haze grinder unit 805 includes a motor 815 that is attached to a gear assembly 820. A threaded shaft 825 is mechanically coupled to the gear assembly 820 at a proximal end of the threaded shaft 825. The threaded shaft 825 is placed through an insulated bowl housing 830, a screen 835, and a bearing 840. At a distal end of the threaded shaft 825, it is attached to rotating grinding teeth 845 by way of threads on the external surface of the shaft 825 and in the bore of the rotating grinding teeth 845. A bowl structure 850 receives the rotating grinding teeth 845 therein at the bottom surface of the bowl structure 850. A bowl lid 855 covers the top of the bowl structure 850 and a seal 860 seals the bowl lid 855 to the bowl structure 850. A power source 810, e.g., batteries, can power the motor 815.

FIG. 9 is a cross-sectional view of an assembled vaporizer 800 having an integrated grinder unit 805 in accordance with an embodiment of the invention. The threaded shaft 825 is driven by the mother 815 (FIG. 8), which in turn drives the rotating grinding teeth 845 inside the vaporization chamber 850. The bearing 840 facilitates rotating of the grinding teeth 845 while keeping the insulated bowl housing 830 and bowl structure 850 stationary. The insulated bowl housing 830 has slots, which are engaged by extensions of the bowl structure 850 to form an anti-rotation feature. The bowl lid 855 includes slots that can be engaged by a part of an outer housing (not shown) of the vaporizer 800. The bowl structure 850 and the bowl lid 855 include stationary teeth 910 and stationary grinding surfaces 905, respectively, which function in conjunction with the rotating grinding teeth 845 to grind the contents inside the bowl structure 850.

In general, the vaporizer 800 integrates motor driven grinding teeth 845 at the vaporization chamber 0. Herbs (not shown) can be placed into the vaporization chamber 850 in their natural state (unground). The vaporizer 800 can grind the material from within the vaporization chamber 850 ensuring all particles (big and small) stay within the vaporization chamber 850. This method bypasses the usual step of transferring ground herb from grinder to vaporization unit where loss of particles can occur. By integrating the grinder into the vaporization chamber no herbal material is lost from its unground state. Heating elements 920 can be activated during, after or before grinding as the systems are independent of each other.

This description has been presented for purposes of illustration and description. It is not intended to be exhaustive or to limit the disclosure to the precise forms disclosed. Obvious modifications or variations are possible in light of the above teachings. The embodiments discussed, however, were chosen to illustrate the principles of the disclosure, and its practical application. The disclosure is thus intended to enable one of ordinary skill in the art to use the disclosure, in various embodiments and with various modifications, as are suited to the particular use contemplated. All such modifications and variation are within the scope of this disclosure, as determined by the appended claims when interpreted in accordance with the breadth to which they are fairly and legally entitled.

Therefore, having thus described the disclosure, at least the following is claimed:

1. A vaporizer comprising:
a power source;
a heating element that is electrically coupled to the power source;
multiple chambers that are coupled to the heating element and are configured to vaporize a substance that is placed within the multiple chambers;
an inner tube that is coupled to the multiple chambers and is configured to allow the vaporized substance to exit therefrom;
a housing that houses the power source, heating element, inner tube, and multiple chambers;
a chamber container that contains the multiple chambers and includes extending bars that align corresponding holes at the inner tube, wherein each extending bar has a borehole that creates an air path from the multiple chambers to the inner tube; and
a lever structure that rotates the inner tube to align and misalign the corresponding holes at the inner tube with the extending bars of the chamber container.

2. The vaporizer as defined in claim 1, wherein the chamber container isolates each chamber from another such that the vaporized substance from one chamber does not enter into another chamber.

3. The vaporizer as defined in claim 1, further comprising a switch that connects the power source to the heating element, wherein the lever structure turns the switch to a left direction and a right direction, which in turn connects the power source to the heating element corresponding to one of the multiple chambers.

4. The vaporizer as defined in claim 1, further comprising a push button that connects the power source to a chip assembly.

5. The vaporizer as defined in claim 4, wherein the chip assembly is designed to power on and adjust the temperature of the heating element responsive to the number of times the push button is pushed.

6. The vaporizer as defined in claim 1, further comprising a mouth piece that extends from the inner tube.

7. The vaporizer as defined in claim 6, wherein the lever structure covers the mouth piece in an off position and uncovers the mouth piece in an on position.

8. The vaporizer as defined in claim 1, further comprising an outer tube that contains the inner tube, forming an incoming air path between the outer tube and inner tube.

9. The vaporizer as defined in claim 8, wherein the inner tube conducts heat from the vaporized substance and transfers the heat to an incoming air in the incoming air path.

10. A vaporizer comprising:
a power source;
a heating element that is electrically coupled to the power source;
at least one chamber that is coupled to the heating element and is configured to vaporize a substance that is placed within the at least one chamber;
an inner tube that is coupled to the at least one chambers and is configured to allow the vaporized substance to exit therefrom;

an outer tube that contains the inner tube, forming an incoming air path between the outer tube and inner tube;

a housing that houses the power source, heating element, inner tube, outer tube, and at least one chambers, wherein the inner tube conducts heat from the vaporized substance and transfers the heat to an incoming air in the incoming air path;

a chamber container that contains the at least one chamber and includes extending bars that align corresponding holes at the inner tube, wherein each extending bar has a borehole that creates an air path from the at least one chamber to the inner tube; and a lever structure that rotates the inner tube to align and misalign the corresponding holes at the inner tube with the extending bars of the chamber container.

11. The vaporizer as defined in claim 10, wherein the chamber container isolates each chamber from another such that the vaporized substance from one chamber does not enter into another chamber.

12. The vaporizer as defined in claim 10, further comprising a push button that connects the power source to a chip assembly.

13. The vaporizer as defined in claim 12, wherein the chip assembly is designed to power on and adjust the temperature of the heating element responsive to the number of times the push button is pushed.

14. The vaporizer as defined in claim 10, further comprising a mouth piece that extends from the inner tube.

15. The vaporizer as defined in claim 14, wherein the lever structure covers the mouth piece in an off position and uncovers the mouth piece in an on position.

* * * * *